United States Patent [19]
Overaker et al.

[11] Patent Number: 5,871,127
[45] Date of Patent: Feb. 16, 1999

[54] AUTOMATICALLY-VENTING DISPENSING CAP

[75] Inventors: Ronald F. Overaker, Durham; Brian C. Dodge, Hillsborough; David L. Epstein, Bahama, all of N.C.

[73] Assignee: Duke University, Durham, N.C.

[21] Appl. No.: 835,076

[22] Filed: Apr. 4, 1997

[51] Int. Cl.⁶ .................................................. B65D 37/00
[52] U.S. Cl. ......................... 222/212; 222/422; 222/484; 222/536
[58] Field of Search ...................... 222/212, 529, 222/530, 482, 484, 422, 536; 137/625.47

[56] References Cited

U.S. PATENT DOCUMENTS

| | | |
|---|---|---|
| 2,625,304 | 1/1953 | Mart ...................................... 222/536 X |
| 5,020,526 | 6/1991 | Epstein . |
| 5,065,881 | 11/1991 | Tarng .................................... 222/536 X |
| 5,342,327 | 8/1994 | Epstein . |
| 5,671,868 | 9/1997 | Herr ...................................... 222/536 X |

*Primary Examiner*—Gregory L. Huson
*Attorney, Agent, or Firm*—Clark & Erbing LLP

[57] ABSTRACT

A dispensing cap including a rotary valve communicating with an external open-ended dispensing tube portion, the valve being configured to communicate, in a venting position, with a venting pathway and to communicate, in a dispensing position, with an internal dispensing tube portion, wherein the valve is configured to pass from a closed position through a venting position to a dispensing position.

17 Claims, 3 Drawing Sheets

AUTOMATICALLY-VENTING DISPENSING CAP

BACKGROUND OF THE INVENTION

This invention relates to dispensing liquids.

It is often desirable to administer a liquid medicine to treat a disease (e.g., an infection, inflammation, or glaucoma); to administer water or a buffered fluid to lubricate an eye, whether or not it is covered with a contact lens; or to administer water or a buffered fluid to irrigate an eye that has been contacted with a harmful agent, such as an acid or alkali.

For example, U.S. Pat. No. 5,020,526 relates to a plastically deformable bottle having a target and a lens to aid in positioning the bottle near the eye. Embodiments further include a clip for securing the flexible tube, and a tube which is fixed at an acute angle to the longitudinal axis of the bottle. A related application issued as U.S. Pat. No. 5,342,327 which relates to a bottle which includes a tube extending into and out of the bottle. The external portion of the tube is flexible and extends at an acute angle to the axis of the bottle, thereby allowing a person to administer liquids to his eye without tipping his head. A cushion pad is molded as part of the bottle to prevent accidental injury to the eye from the tip of the external portion of the tube.

SUMMARY OF THE INVENTION

The invention features a dispensing cap for a vessel, e.g., a bottle or a can. The cap includes a seal configured to occlude the vessel, a venting pathway through the seal, an internal dispensing tube portion passing through the seal, and a rotary valve communicating with an external open-ended dispensing tube portion. The valve is configured to communicate, in a venting position, with the venting pathway and to communicate, in a dispensing position, with the internal dispensing tube portion. The valve is configured to pass from a closed position through a venting position to a dispensing position.

Advantages of the disclosed dispensing cap include the automatic venting or equilibration of internal bottle pressure before liquid is dispensed with minimal risk of spilling the liquid. A preferred embodiment is a dispensing cap for a plastically deformable bottle for dispensing liquids into an eye. The disclosed dispensing cap provides a liquid dispenser which dispenses fluid while the bottle and the patient's head each remain in a substantially upright position. The present design also minimizes contamination of the dispensing tip, by enclosing the dispensing tube within the housing which is further secured by a cap. The disclosed cap can be easily adapted and provided for use with existing bottles of generic or standard size, vials, and ampules of liquid medicine, buffered solutions, or water. The rotary valve can be adapted to predetermined angles of rotation, or to ensure that the closed, venting, and dispensing positions are secure.

Other features and advantages of the invention will be apparent from the following figures, description, and from the claims.

DESCRIPTION OF THE PREFERRED EMBODIMENTS

Structure

Figure 1:
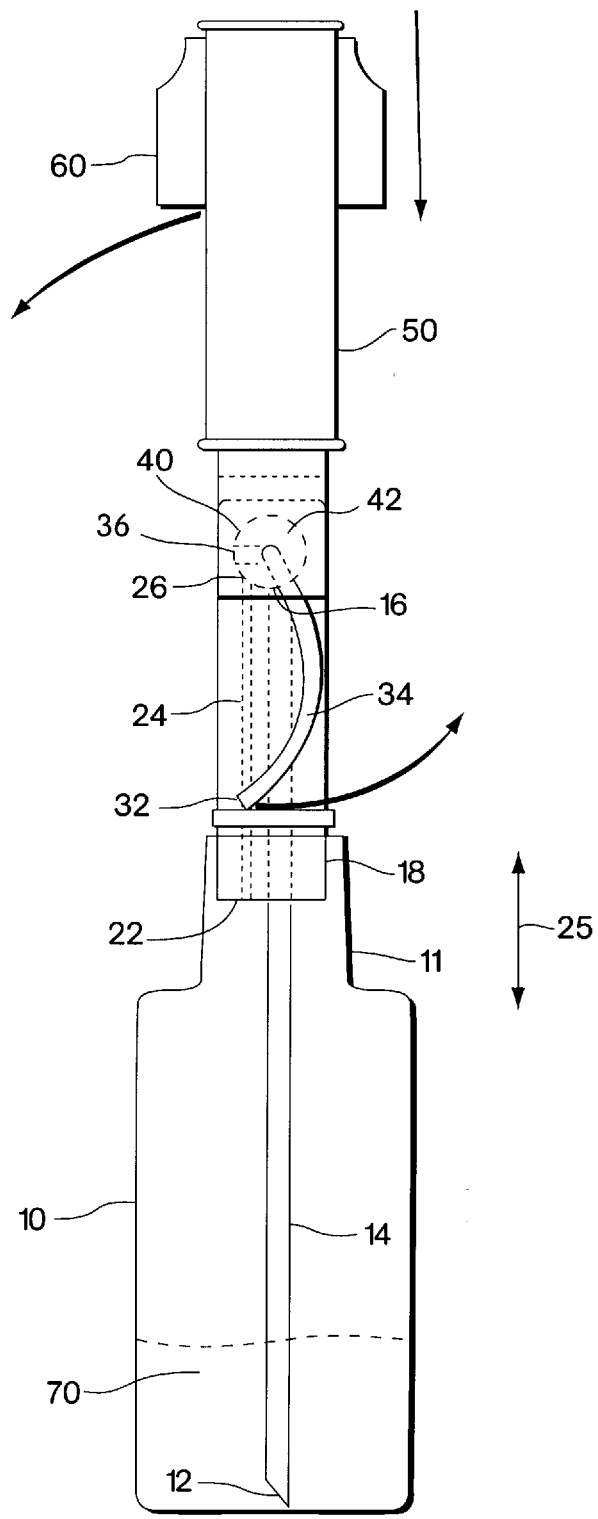
FIG. 1 is a cross-section through a dispensing cap according to the invention and a bottle for dispensing liquid into an eye.

Referring to FIG. 1, bottle 10 is manufactured from a plastically deformable polymeric material, e.g., polypropylene. Bottle 10 is airtight except at the open end 12 of the internal dispensing tube portion 14, and the open end 22 of the venting pathway 24. Internal dispensing tube portion 14 and venting pathway 24 pass through seal 18. Seal 18 prevents liquid leaking inadvertently from bottle 10. Tube portion 14 passes internally nearly the whole length of bottle 10, running parallel to the longitudinal axis 25 of bottle 10. The distal end 16 of internal dispensing tube portion 14 opens onto the chamber 40 of rotary valve 42. Chamber 40 and rotary valve 42 are manufactured (e.g., machined or, preferably, injection molded) from materials which form effective seals and are inert with respect to the liquid to be dispensed. Such pairings include polypropylene, polyethylene, polycarbonate, glass-to-glass, and metal-to-metal seals. Venting pathway 24 passes internally through seal 18, and optionally through the upper portion of bottle 10. In some embodiments, venting pathway 24 is no longer than the neck 11 of bottle 10, or is less than one-half of the length of bottle 10, to allow the internal vapor pressure to equilibrate with the atmospheric vapor pressure when rotary valve 42 is in a venting position. The distal end 26 of venting pathway 24 also opens onto chamber 40 of rotary valve 42.

Rotary valve 42 is airtight except for two open ends. First, rotary valve open end 36 slidably or rotatably contacts with various portions of the interior wall of valve chamber 40, such as distal venting end 26 or distal dispensing end 16. Second, rotary valve 42 communicates with external open end 32 of external dispensing tube portion 34. Valve housing 50 rotates with valve 42. Valve 42 and chamber 40 are enclosed by valve housing 50 during storage. Valve housing 50 is vertically slidable, exposing external dispensing tube portion 34. Sealing cap 60 slides over housing 50 and secures housing 50 to bottle 10 (e.g., by snapping closed or screwing tight). Bottle 10 is preferably cylindrical, and has a volume of between about 5 and 20 ml, but can be up to 100 ml, 150 ml, 300 ml, 500 ml or more. Seal 18 can be, for example, a snap-on seal, a septum, or a screw top. Rotary valve 42 and rotary chamber 40 can be adapted, e.g., with protrusions or depressions, for rotation through preset angles and to ensure that rotary valve open end 36 is centered or aligned with distal venting end 26 or distal dispensing end 16. External dispensing tube 34 can be adapted for dependent rotation with rotary valve 42, or for independent rotation to an angle suitable for each user.

Use

Bottle 10 is manufactured and filled with a sterile medical or wash liquid 70 by standard pharmaceutical procedures.

Bottle 10 is sealed with conventional cap 72 or with a dispensing cap of the invention. Conventional cap 72 may be replaced with a dispensing cap of the invention immediately before use. Liquid 70 remains sterile until either conventional cap 72 or sealing cap 60 is removed. Contamination is prevented by replacement of sealing cap 60 immediately after use.

Figure 2A:
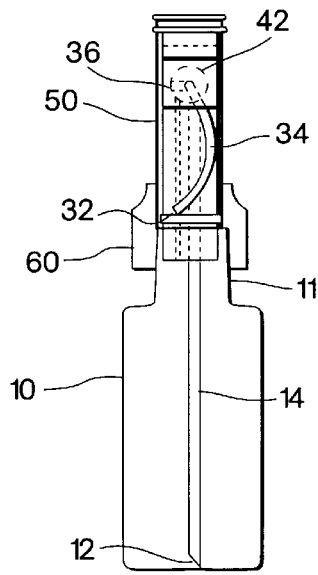
FIGS. 2A–2D are cross-sections through a bottle and a cap of the invention showing (2A) the housing in a closed or housed position, (2B) in use, wherein the slidable housing is in an open position, and the rotary valve is in a closed position, with arrows indicating rotation of the housing and of the external dispensing tube, (2C) in use, wherein the slidable housing rotates with the rotary valve, and the valve is in a venting position, namely, the interior of the bottle is in communication with the external dispensing tube portion and the atmosphere, and (2D) in use, wherein the valve is in a dispensing position, dispensing liquid from the bottle.
Figure 2B:
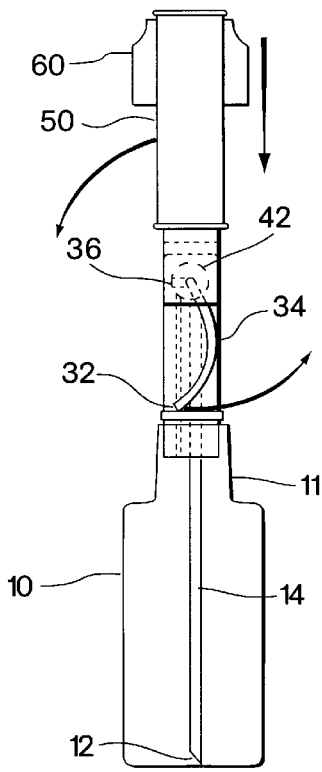

Referring to FIGS. 2A and 2B, to administer one or more drops of liquid 70 from bottle 10, the user removes sealing cap 60, and slides up housing 50 to expose external dispensing tube portion 34. Housing 50 can be configured to reversibly lock in this position. In a first, closed position, valve open end 36 communicates with the wall of chamber 40.

Figure 2C:
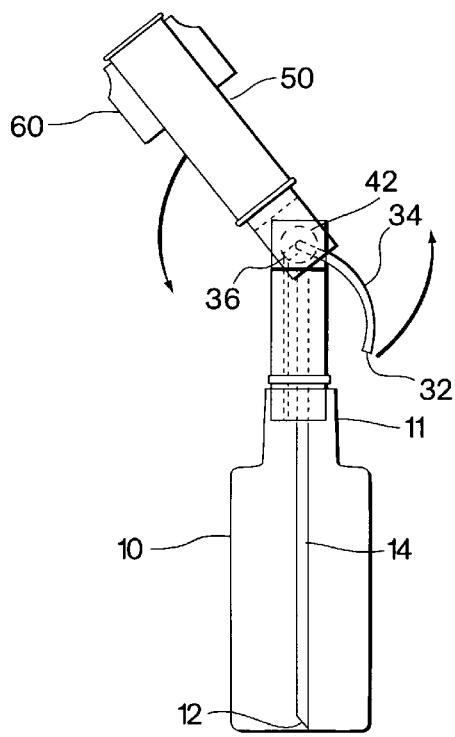

Referring to FIG. 2C, the user can hold housing 50 and thereby rotate rotary valve 42 from the first closed position until valve open end 36 communicates with distal end 26 of venting pathway 24 in a second venting position. This second venting position allows the internal bottle pressure to equilibrate with the atmospheric pressure.

Figure 2D:
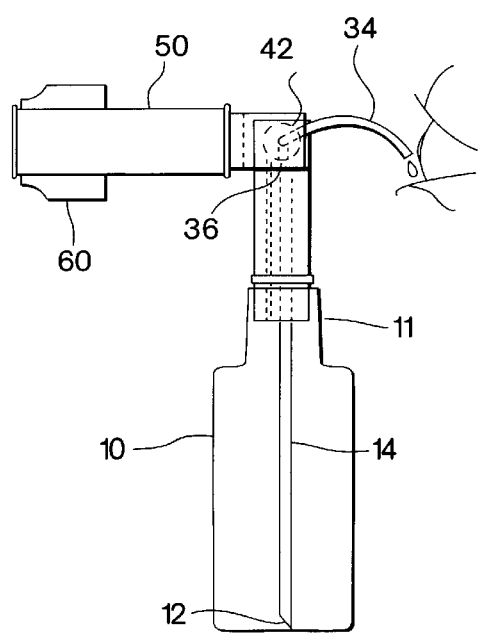

Referring to FIG. 2D, the user rotates rotary valve 42 until valve end 36 communicates with distal end 16 of internal dispensing tube portion 14 in a third dispensing position. In this dispensing position, the user can squeeze bottle 10 to cause the liquid in bottle 10 to pass through internal dispensing tube portion 14 and external dispensing tube portion 34 and out external open end 32 into, e.g., the eye. Preferably, internal dispensing tube portion 14 is a dip tube which extends to the bottom of bottle 10, thereby allowing dispensation of liquid 70 without inverting or substantially tilting bottle 10.

Figure 3:
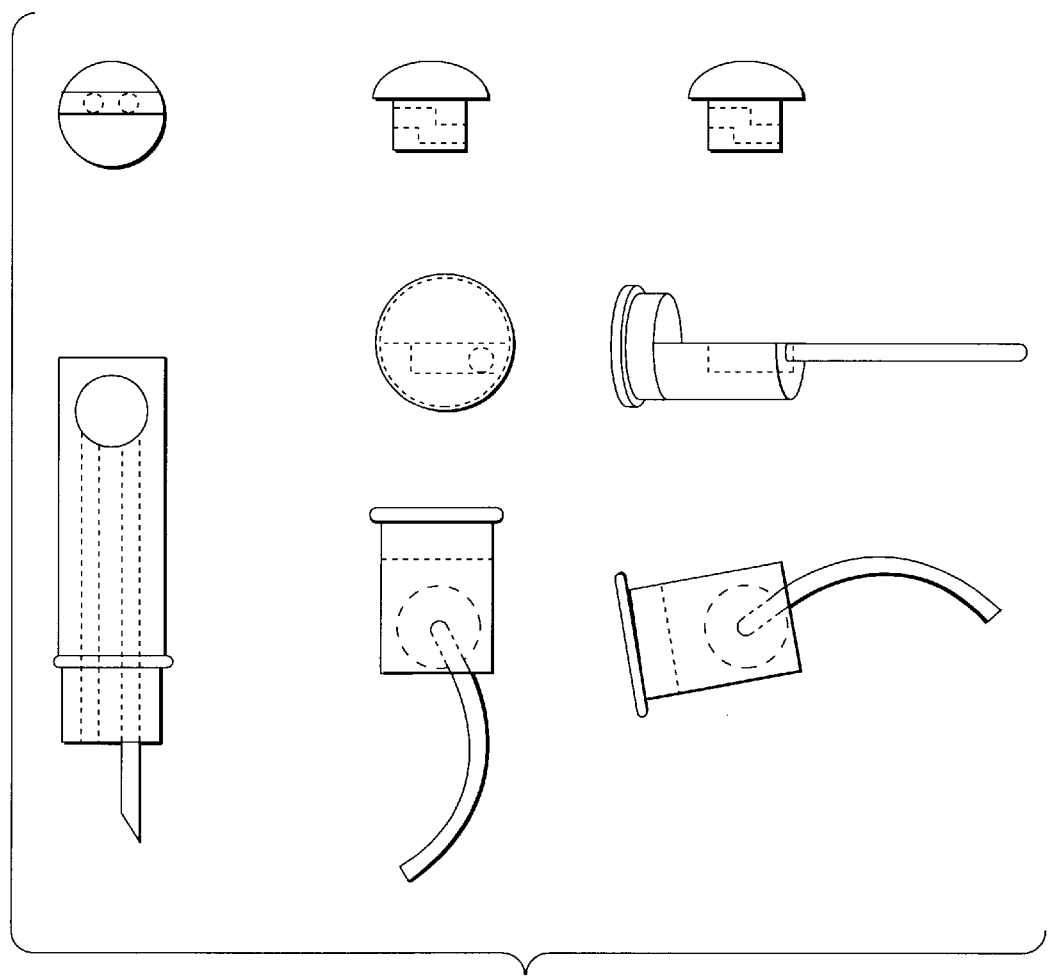
FIG. 3 is a view of components from which one cap embodiment of the invention is assembled.

In one embodiment, rotary valve 42 and rotary valve chamber 40 are configured such that in use, rotary valve open end 36 passes from a closed position (wall of rotary chamber 40) through a second position aligned with distal venting end 26 to a third position aligned with distal dispensing end 16. After dispensing liquid 70, the user holds housing 50 and rotates valve 42 in the reverse direction, so rotary valve open end 36 passes from alignment with distal dispensing end 16 through alignment with distal venting end 26 to a closed position against the wall of valve chamber 40. Alternatively, valve 42 and chamber 40 can be configured such that after dispensing liquid 70, valve open end 36 passes from alignment with distal dispensing end 16 directly to a closed position against the wall of valve chamber 40 without communicating with distal venting end 26, or communicating the interior of the bottle with the external dispensing tube portion. Referring to FIG. 3, components of one embodiment of the invention are shown. These can be manufactured by machining or, preferably, by injection molding.

In another embodiment (not shown), bottle 10 has two liquid reservoirs, e.g., a liquid medicine and a sterile saline buffer, or a first and a second liquid medicine. The dispensing cap includes a first internal dispensing tube portion 14 which extends into a first liquid reservoir, and a second internal dispensing tube portion which extends into a second liquid reservoir. Rotary valve chamber 40 has at least three ports, namely, distal venting end 26, first distal dispensing end 16, a second distal dispensing end, and an optional second distal venting end. If the second liquid reservoir is a sterile saline buffer or water, the second distal venting end may not be necessary. For example, equalizing the internal vapor pressure of the saline buffer or water is not as critical when the second liquid reservoir is intended to rinse the external dispensing tube portion before storage, or to administer nonspecific volumes of saline or water into the eye.

Analogously, bottle 10 can have three liquid reservoirs, a first liquid medicine, a sterile saline solution, and a second liquid medicine. After dispensing an aliquot of the first liquid medicine, the user can dispense a rinsing volume of the sterile saline solution to clean the external dispensing tube portion before storage, or before dispensing an aliquot of the second liquid medicine.

Other Embodiments

Other embodiments are within the following claims. For example, larger versions of bottle 10 can be used to irrigate eyes with a continuous flow of liquid. In such bottles end 32 of tube 34 would be wider to allow for the greater flow.

Snap-on caps as well as screw-on caps can be used to cover end 32. The bottle can have a shape other than cylindrical.

The cap of the invention, or a bottle having a cap of the invention, can have other features, including a protrusion adapted to cooperate with the open end 32 such that when the protrusion is rested against the face of a human below the eye, open end 32 is located adjacent to the eye, and a target coupled to bottle 10 as an aid in positioning the open end near the eye, as disclosed in U.S. Pat. No. 5,020,526 and in U.S. Pat. No. 5,342,327, each of which is hereby incorporated by reference. The protrusion can be a chin rest portion or, preferably, a cheek rest portion.

The disclosed dispensing cap can also be modified for use with nonophthamological liquids. Gas and liquid mixtures in closed systems can produce pressures higher (or lower) than atmospheric pressure in a variety of contexts. Examples include a Dewar flask, a thermos, or other presssure-resistant chamber containing heated or cooled fluids (e.g. liquid nitrogen, liquid helium, supercritical fluids, hot water or aqueous solutions), fluids with high vapor pressures such as ammonia-based cleaning fluids and hydrocarbons such as gasoline, and fluids or mixtures containing solvated gases under pressure, such as carbonated beverages, separatory funnel mixtures, or the contents of chromatography columns. The disclosed dispensing cap can also be used with collapsible or compressible plastic vessels, such as those used for photographic developing solutions or transportation of fluids.

What is claimed is:

1. A dispensing cap for a plastically deformable bottle for dispensing liquid into an eye of a human, said cap comprising:
   a seal configured to occlude said bottle,
   a venting pathway through said seal,
   an internal dispensing tube portion passing through said seal, and
   a rotary valve communicating with an external open-ended dispensing tube portion, said valve being configured to communicate, in a venting position, with said venting pathway and to communicate, in a dispensing position, with said internal dispensing tube portion, wherein said valve is configured to pass from a closed position through a venting position to a dispensing position.

2. A dispensing cap of claim 1, further comprising a housing which slidably encloses said rotary valve in a first, closed position wherein said valve does not communicate with either said venting pathway or said internal dispensing tube portion.

3. A dispensing cap of claim 2, wherein said housing is slidably removable.

4. A dispensing cap of claim 2, wherein said housing rotates with said rotary valve.

5. A dispensing cap of claim 2, further comprising a sealing cap which slides over said housing, thereby securing the housing.

6. A dispensing cap of claim 1, wherein said seal is a snap seal.

7. A dispensing cap of claim 1, wherein the angle of rotation of said rotary valve is variable.

8. A dispensing cap of claim 1, wherein said rotary valve is adapted to rotate through preset angles.

9. A dispensing cap of claim 1, wherein said rotary valve is configured to rotate after use from said dispensing position through a venting position to a closed position.

10. A dispensing cap of claim 1, wherein said internal dispensing tube portion comprises a dip tube which extends to the bottom of the bottle.

11. A dispensing cap of claim 1, wherein said venting pathway comprises a venting tube.

12. A dispensing cap of claim 1, wherein said internal dispensing tube portion is a first internal dispensing tube portion, further comprising a second internal dispensing tube portion, such that in a second venting position said rotary valve communicates with said second internal dispensing tube portion.

13. A dispensing cap of claim 1, wherein said external dispensing tube rotates with said rotary valve.

14. A dispensing cap of claim 1, further comprising a means for regulating the volume of liquid dispensed.

15. A bottle for dispensing liquid into an eye of a human, comprising:
   a plastically deformable bottle, and
   a cap comprising:
      a seal configured to occlude a bottle,
      a venting pathway through said seal,
      an internal dispensing tube portion passing through said seal, and
      a rotary valve communicating with an external open-ended dispensing tube portion, said valve being configured to communicate, in a venting position, with said venting pathway and to communicate, in a dispensing position, with said internal dispensing tube portion, wherein said valve is configured to pass from a closed position through a venting position to a dispensing position.

16. A bottle of claim 15, further comprising a chin rest or a cheek rest adapted to anchor said bottle or said external dispensing tube during use.

17. A bottle of claim 15, wherein said bottle interior is a first reservoir, and said liquid is a first liquid, further comprising a second reservoir for a second liquid, and wherein said internal dispensing tube portion is a first internal dispensing tube portion, further comprising a second internal dispensing tube portion, such that in a second venting position said rotary valve communicates with said second internal dispensing tube portion, wherein squeezing the bottle to deform it causes the second liquid to pass through said second internal dispensing tube portion and out the open end of said external dispensing tube portion.

* * * * *